Aug. 25, 1964 R. G. JELLY Plant Pat. 2,443
ROSE PLANT
Filed Oct. 18, 1963
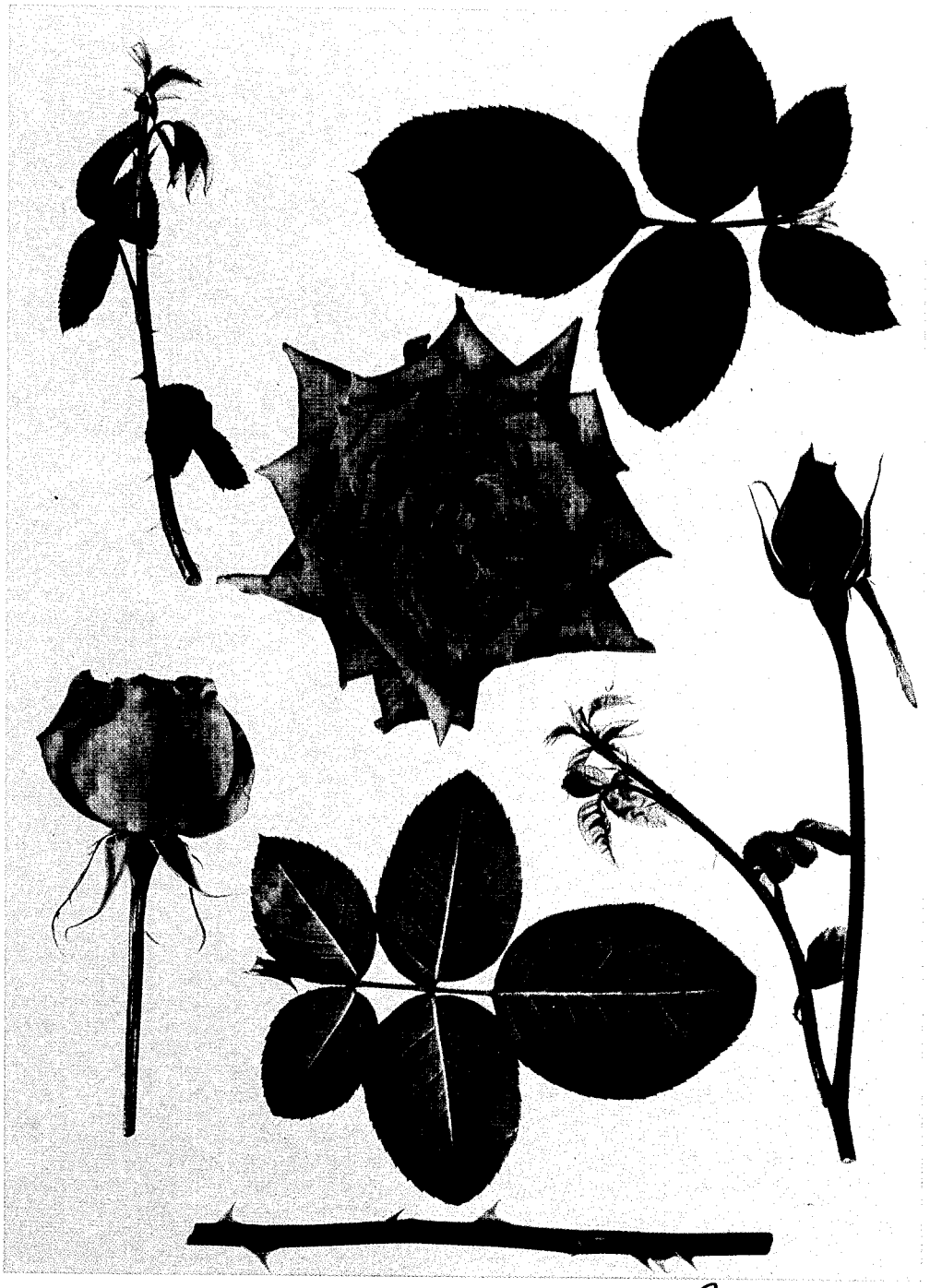
Inventor.
Robert G. Jelly
By: Robb & Robb
Attorneys.

United States Patent Office

Plant Pat. 2,443
Patented Aug. 25, 1964

2,443
ROSE PLANT

Robert G. Jelly, Richmond, Ind., assignor to E. G. Hill Co., Inc., Richmond, Ind., a corporation of Indiana Filed Oct. 18, 1963, Ser. No. 317,394
1 Claim. (Cl. Plt.—20)

The present invention relates to a new and distinct variety of rose plant of the hybrid tea class, which was originated by me by crossing the variety "Yuletide" (Plant Patent No. 1,391) with an unnamed and unpatented seedling identified in my breeding records as #1–57–R.

The primary objective of this breeding was to produce a new rose variety in which there is combined the vigor and growth habits of the unnamed pollen parent, and the keeping quality and flower color of the seed parent "Yuletide." This objective was fully achieved along with other desirable improvements, as evidenced by the following unique combination of characteristics which are outstanding in the new variety and which distinguish it from its parents, as well as from all other varieties of which I am aware:

(1) Vigorous and upright habits of growth;
(2) Good flower productivity;
(3) Long, pointed buds, with stiff and erect necks;
(4) A distinctive and attractive red flower color;
(5) Excellent keeping quality of the flowers as cut flowers.

In comparison with its seed parent "Yuletide," the new variety represents a substantial improvement thereover, as particularly attributed to the longer and more pointed buds of the new variety, said buds having stiffer and more erect necks. In addition, the new variety has better flower productivity.

As compared with its unnamed pollen parent, the new variety has better flower keeping qualities, and has retained the good keeping qualities of the seed parent "Yuletide."

The new variety more nearly resembles "Yuletide" than any other variety, but "Yuletide" has longer canes and produces shorter buds with weaker necks. The flower color of the new variety is somewhat similar to that of "Happiness" (Plant Patent No. 911), but "Happiness" has longer and heavier canes, with many thorns, and that variety is not an efficient producer of blooms, particularly during periods of low light intensity as usually occur in the winter months of January and February.

Asexual reproduction of the new variety by grafting as performed at Richmond, Indiana, shows that the foregoing characteritsics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert Ridgway's Color Standards and Nomenclature (hereinafter abbreviated as (R)), Robert S. Wilson's Horticultural Colour Chart (hereinafter abbreviated as (W)), Nickerson Color Fan (hereinafter abbreviated as (N)), and Koster's Color Guide (hereinafter abbreviated as (K)), as indicated, except where general color terms of ordinary dictionary significance are obvious:

Type: Seedling; greenhouse; for cut flowers.
Class: Hybrid tea.
Breeding: Seedling.
*Seed parent.*—"Yuletide."

*Pollen parent.*—An unnamed seedling identified as #1–57–R.

Propagation: Holds its distinguishing characteristics through succeeding propagations by grafting.

*Flower*

Locality where grown and observed: Richmond, Indiana.
Flowers borne: One to a stem; on strong stems of from medium to long length.
Quantity of bloom: Abundant, in greenhouse.
Continuity: Continuous, in greenhouse.
Fragrance: Penetrating, in greenhouse. Nature—spicy.
Bud:
*Peduncle.*—Medium length; from large to medium diameter; erect; strong. Bark—slightly rough, due to numerous minute prickles of Sulphur Yellow color, Plate 1/3 (W); no thorns or hairs. Color—Moderate Yellow Green, Plate 5GY 5/6 (N), shaded to Strong Yellow Green, Plate 5GY 6/8 (N) at base of bud.
*Before calyx breaks.*—Size—medium. Form—long-pointed; with a conspicuous neck; with foliaceous appendages on the surface of the bud; with much-cut bristle-like foliaceous parts extending beyond the tip of the bud equal to ¾ or more of its length. Color—shaded from Moderate Yellow Green, Plate 2.5GY 5/5 (N) at base to Spinach Green, Plate 0960/2 (W).
*As calyx breaks.*—Color (outside)—Ruby Red, Plate 827 (W).
*As first petal opens.*—Size—medium. Form—long pointed. Color: outside—shaded from Cardinal Red, Plate 822/2 (W) to lighter and darker hues, with Uranium Green, Plate 63/3 (W) at base; inside—Cardinal Red, Plate 822/3 (W), with Chrome Yellow, Plate 605/3 (W) and venation at base.
*Opening.*—Opens up well in greenhouse; slight decrease in flower and bud size during hot, dry weather.
Bloom:
*Size (when fully open).*—Large; from 4 inches to 5½ inches.
*Petalage.*—Very double; from 32 to 45 petals; arranged regularly.
*Form.*—Full and high-centered at first, but becoming from flat to slightly high-centered; petals being at first tightly rolled inward but later becoming rolled outward at maturity.
Petals:
*Texture.*—Moderate thickness.
*Appearance.*—Inside—velvety. Outside—satiny.
*Shape.*—Outer—from oval to obovate, with apex flat and with one slight apical point. Intermediate—from oval to slightly obovate, with apex from flat to slightly mucronate, and with one notch. Inner—slightly obovate, with apex having one apical point.

This description of a newly opened flower was made from a rose grown in a greenhouse during the month of July at Richmond, Indiana.

*Color.*—Outer petal: outside surface—Cardinal Red, Plate 822/3 (W), with a suffusion of Rose Red, Plate 724/1 (W), and Naples Yellow, Plate 403/2 (W) at base; inside surface—Cardinal Red, Plate 822/3 (W), with Naples Yellow, Plate 403 (W) at base. Intermediate petal: outside surface—Cardinal Red, Plate 822/2 (W) with Sulphur Yellow, Plate 1/3 (W) at base; inside surface—Brighter and deeper than Cardinal Red, Plate 822/2 (W), shaded to Currant Red, Plate 821/3 (W) toward base, and with a small area of Egyptian Buff, Plate 407/1 (W) at base. Inner petal: outside surface—brighter and deeper than Cardinal Red, Plate 822/2 (W), due to its velvety texture, shaded to Cardinal Red, Plate 822/1 (W) near base, with Massicot Yellow, Plate XVI (R) at base; inside surface—Cardinal Red, Plate 822 (W) with Massicot Yellow, Plate XVI (R) at base.

This description was made from a rose that was open for three days in a greenhouse during the month of July at Richmond, Indiana.

*Color.*—Outer petal: outside surface—Rose Red, Plate 724 (W), with Amber Yellow, Plate 505/3 (W) at base; inside surface—Rose Red, Plate 724 (W), shaded to Spirea Red, Plate 025/1 (W), with Amber Yellow, Plate 505/3 (W) at base. Intermediate petal: outside surface—China Rose, Plate 024 (W), with Chrome Yellow, Plate 605/3 (W) at base; inside surface—Rose Red, Plate 724/1 (W), with Chrome Yellow, Plate 605/2 (W) at base. Inner petal: outside surface—Spirea Red, Plate 025/1 (W), with Chrome Yellow, Plate 605/3 (W) at base; inside surface—China Rose, Plate 024 (W), with Chrome Yellow, Plate 605/2 (W) at base.

*General color effect.*—Newly opened flower—brighter than, but nearest, Cardinal Red, Plate 822/3 (W). Three days open—Rose Red, Plate 724/1 (W).

*Behavior.*—Petals persist in greenhouse; during hot, dry weather, blooms are smaller in size and change faster from Cardinal Red to China Red and Rose Red, fading to Rose Red, Plate 724/2 (W).

*Flower longevity.*—Cut flowers grown in greenhouse and kept at living room temperatures—6 days in July.

*Plant*

Foliage:

*Leaves.*—Compound of 3–5 leaflets; normal abundance; medium size; moderately thin and smooth; some showing a light satiny shine.

*Leaflets.*—Shape—varies from almost oval to almost elliptical. Apex—cuspidate. Base—from obtuse to oblique. Margin—very finely serrate.

*Color.*—Mature: upper surface—some venation as dark as Elm Green, Plate XVII (R), but in general darker than Forest Green, Plate XVII (R), but not as dark as Elm Green, Plate XVII (R); under surface—slightly greyer than Cedar Green, Plate 80 (K). Young: upper surface—just as young growth shows bud, main vein Dark Red, Plate 5R 3/7 (N), as well as suffusion along serrate edge, with leaf generally Cress Green, Plate XXXI (R); under surface—just as young growth shows bud, Sage Green, Plate 78 (K), with venation and suffusion of Pompeian Red, Plate XIII (R).

*Rachis (the supporting stem of the compound leaf).*—Medium. Upper side—grooved; prickly. Under side—prickly.

*Stipules.*—From short to medium length; narrow; with points from short to medium length turning out at an angle of less than 90°.

Growth (in greenhouse):

*Habit.*—Upright; much-branched.

*Growth.*—Free; vigorous.

*Canes.*—From large to medium diameter.

*Main stems.*—Color—varies from Spinach Green, Plate 0960/2 (W) to Parsley Green, Plate 00962/2 (W). Thorns—several; medium length; hooked very slightly downward; with narrow base; color—shaded from Dark Orange Yellow, Plate 7.5YR 6/9 (N) to strong Yellowish Brown, Plate 7.5YR 5/7 (N). Prickles—few; color—Mimosa Yellow, Plate 602/3 (W). Hairs—none.

*Branches.*—Color—varies from Spinach Green, Plate 0960/3 (W) to Spinach Green, Plate 0960 (W), with irregular stemspots of Fern Green, Plate 0862/2 (W); characteristic stem spotting is not common to rose varieties in general. Thorns—from few to several; medium length; hooked slightly downward; with narrow, elongated base; color—shaded from Pod Green, Plate 061/1 (W) to Pod Green, Plate 061 (W) at tip, with Ecru-Olive base, Plate XXX (R). Prickles—several near base of individual canes; color—Baryta Yellow, Plate IV ((R). Hairs—none.

*New shoots.*—Color—Spinach Green, Plate 0960/3 (W), with irregular stemspots varying from Pea Green, Plate 61/3 (W) to Pea Green, Plate 61/2 (W) just before the new shoot shows bud. Thorns—from few to several; medium length; hooked slightly downward; with narrow base; color—Pod Green, Plate 061 (W), suffused with Brick Red, Plate XIII (R), and with tip Pod Green, Plate 061 (W). Prickles—several near base of cane; color—Brick Red, Plate XIII (R). Hairs—none.

*Reproductive Organs*

Stamens: Medium number; arranged regularly about pistils; tucked in calyx.

Filaments: From short to medium length; most with anthers. Color—Rose Red, Plate 724/3 (W).

Anthers: Medium size; open at various times. Color—Rose Red, Plate 724/3 (W).

Pollen: Moderate quantity. Color—Strong Orange, Plate 5YR 7/11 (N).

Pistils: Medium number.

Styles: Uneven; from short to medium length; moderately thin; loosely bunched. Color—Spinel Red, Plate 0023 (W), with base shaded from Indian Yellow, Plate 6/3 (W) to Indian Yellow, Plate 6/2 (W).

Stigma: Color—Egyptian Buff, Plate 407/3 (W).

Ovaries: Some protruding from calyx.

Hips: Long; flat at top; oblong shape; with conspicuous neck; generally urn-shaped, with flat top and almost V-shaped at base; moderately smooth; walls from medium thickness to thick and fleshy. Color—slightly darker than Strong Orange, Plate 5YR 7/11 (N).

Seeds: Many; medium size.

I claim:

A new and distinct variety of rose plant of the hybrid tea class, substantially as herein shown and described, characterized particularly as to novelty by the unique combination of vigorous and upright habits of growth, good flower productivity, long, pointed buds, with stiff and erect necks, a distinctive and attractive red flower color, and excellent keeping quality of the flowers as cut flowers.

No references cited.